(12) United States Patent
Filly et al.

(10) Patent No.: US 6,379,307 B1
(45) Date of Patent: Apr. 30, 2002

(54) ADJUSTABLE NEEDLE GUIDE APPARATUS AND METHOD

(76) Inventors: Roy Filly; Roy Gordon, both of UCSF Medical Center/Room L374, San Francisco, CA (US) 94143-0628; Brett Severence, 102 First St., Kalona, IA (US) 52247-9589

(*) Notice: Subject to any disclaimer, the term of this patent is extended or adjusted under 35 U.S.C. 154(b) by 0 days.

(21) Appl. No.: 09/154,786

(22) Filed: Sep. 16, 1998

(51) Int. Cl.$^7$ ................................................ A61B 8/14
(52) U.S. Cl. ............................................................ 600/461
(58) Field of Search ............................... 606/148, 130, 606/131, 1, 108; 604/116, 93, 72; 600/641, 446, 461; D24/130

(56) References Cited

U.S. PATENT DOCUMENTS

| | | |
|---|---|---|
| 4,058,114 A | 11/1977 | Soldner |
| 4,108,165 A | 8/1978 | Kopp et al. |
| 4,289,139 A | 9/1981 | Enjoji et al. |
| 4,363,326 A | 12/1982 | Kopel |
| 4,402,324 A | 9/1983 | Lindgren et al. |
| 4,408,611 A | 10/1983 | Enjoji |
| 4,469,106 A | 9/1984 | Harui |
| 4,489,730 A | 12/1984 | Jingu |
| 4,491,137 A | 1/1985 | Jingu |
| 4,504,269 A | 3/1985 | Durand |
| 4,542,747 A | 9/1985 | Zurinski et al. |
| 4,608,989 A * | 9/1986 | Drue ........................ 128/660 |
| 4,635,644 A | 1/1987 | Yagata |
| 4,742,829 A | 5/1988 | Law et al. |
| 4,838,506 A | 6/1989 | Cooper |
| 5,052,396 A * | 10/1991 | Wedel et al. ............. 128/662.5 |
| 5,076,279 A * | 12/1991 | Arenson ................... 128/662.5 |
| 5,235,987 A * | 8/1993 | Wolfe ....................... 128/662.5 |
| 5,623,931 A | 4/1997 | Wung et al. |
| 5,752,962 A | 5/1998 | D'Urso |
| 5,758,650 A * | 6/1998 | Miller et al. ............. 128/662.5 |
| 5,941,889 A * | 8/1999 | Cermak ..................... 606/130 |

* cited by examiner

*Primary Examiner*—Gary Jackson
(74) *Attorney, Agent, or Firm*—Merchant & Gould P.C.

(57) ABSTRACT

A needle guide for use in imaging analysis having a body with a slot in it. The slot in the body is configured to receive a needle shaft, the slot having first and second interior surfaces positioned opposite one another and configured to retain the needle shaft between the first and second surfaces along a length of the slot. The slot defines a plane of movement in which the angle of the needle can be adjusted.

24 Claims, 5 Drawing Sheets

ADJUSTABLE NEEDLE GUIDE APPARATUS AND METHOD

FIELD OF THE INVENTION

The present invention relates to a needle guide for a medical imaging instrument. More particularly, the invention is directed to an apparatus and method for guiding needles into selected locations of a patient relative to a medical instrument imaging sensor. The needle guide facilitates entry of a needle through the skin of a patient at an initially obtuse angle to the skin, and then allows the needle to be directed into the patient at a more acute angle after the skin has been pierced.

BACKGROUND

Imaging instruments, such as ultrasound probes, computed tomography scanners (CT Scanners), and magnetic resonance imagers (MRI) have revolutionized the manner in which many important medical procedures are performed. Each of these medical instruments utilizes substantially non-invasive imaging techniques to explore and assess the condition of sub-dermal tissue. As a result of these non-invasive imaging techniques, diagnostic and therapeutic protocol's have been developed that allow for the provision of many highly successful and safe procedures that can be performed with a minimum of disturbance to patients.

Ultrasound, for example, has received widespread acceptance as a useful diagnostic tool. Ultrasound is particularly well suited for obstetrics, where real-time scanners create a continuous image of a moving fetus that can be displayed on a monitoring screen. The image is created by emission of very high frequency sound waves from a transducer placed in contact with the mother's skin. Repeated arrays of ultrasonic beams scan the fetus and are reflected back to the transducer, where the beams are received and the data transmitted to a processing device. The processing device analyzes the information and composes a picture for display on the monitoring screen. Relative measurements may be made, and the gestational age, size and growth of the fetus can be determined. In some circumstances, a needle is guided into amniotic fluid in order to retrieve a fluid sample for analysis. These samples can be useful for diagnosing irregular conditions and can indicate that prenatal care is necessary for the fetus.

Ultrasound probes, and other imaging instruments, are also used for a variety of other purposes, such as identifying the existence, location, and size of tumors, as well as the existence of other medical conditions, including the atrophy or hypertrophy of bodily organs. Ultrasound probes are also useful for inserting catheters into blood vessels and bodily organs. While many imaging techniques are primarily performed on humans, similar techniques are often used by veterinarians to diagnose and treat animals, such as sheep, cows, horses, and pigs.

For many imaging applications, it is desirable that a needle, biopsy instrument, catheter, or other thin instrument (hereafter generalized as "needle" or "needles") be inserted into the body of a patient in order to remove a biopsy sample or to perform other medical procedures. It is normally desirable that the needle be guided to a specific position within the body of the patient. Various guide devices have been designed for assisting in directing the needle. Many of these guides are fixed-angle devices with limited functionality because they have limited control over needle placement compared to a guide that would allow selection of multiple angles. In addition, many of these devices do not permit the placement of more than one needle into a patient or they do not make such multiple placements easy.

One particular problem with many needle guide devices is that they do not permit the needle to readily change angular direction during insertion into the skin or after insertion through the skin of a patient. Thus, such prior art devices allow each needle to assume only one angle with respect to the skin. This single angle can be problematic when the needle is desirably inserted at one angle but is then preferably advanced deeper into a patient at a different angle after the skin has been pierced. Although some prior art systems allow the needle to be removed from the needle guide during adjustment of the angle, this can be a clumsy and uncomfortable undertaking.

The problem of changing the needle angle is particularly pronounced in circumstances when it is desired to direct the needle into a shallow target just below the surface of the skin. Such placement is problematic because the needle must be fixed at a relatively acute angle to the skin and this acute angle means that the needle must pass through a greater distance of skin than would be passed through if the angle were more obtuse. Thus, it would be advantageous to be able to direct the needle into the skin at a first angle that is relatively obtuse to the skin surface and then change the angle to be relatively acute in order to penetrate to the shallow target. Unfortunately, most existing needle guides do not allow the angle to easily change during a medical procedure.

Another specific problem with many current needle guide systems is that they are not well suited to be used with a sterile cover, such as a latex film, placed over the imaging instrument. Such covers are increasingly desirable in order to maintain the ultrasound sensor in a sterile environment. The covers reduce the likelihood of contamination between patients and reduce the cost of medical procedures by minimizing sterilization costs. One challenge of working with latex and similar polymer based covers is that they have a high coefficient of friction and are subject to binding when in contact with moving pieces of an imaging sensor or needle guide. Such binding can lead to tears or punctures of the cover. For example, some prior art imaging sensors have removable pieces that are frictionally fit over a latex cover. Such designs are problematic because they can be difficult to fit and remove, as well as cause problems with binding and an ensuing risk of tearing.

Consequently, a need exists for an improved needle guide system. Such improved needle guide system should permit a needle to be directed into a patient at a variety of angles and allow for the easy removal of the needle from the system without damage to a protective cover.

SUMMARY OF THE INVENTION

The present invention is directed to a needle guide system for use in guiding a needle into a patient who is undergoing imaging analysis. The needle guide includes a body having a slot into which is placed a needle shaft. The slot has two interior surfaces that are positioned opposite one another and combine to define a plane of movement in which the needle can pivot. The needle stays within this plane while being inserted into the patient, but can be freely tilted within the plane, and thus can take numerous angles relative to the surface of the skin. With the present invention, the angle of the needle can change, yet the point at which the needle contacts the skin of a patient can remain the same. Thus, the needle can rotate along a pivot point at the spot where the needle comes in contact with the skin.

In certain implementations, the plane of movement is substantially perpendicular to the surface of the skin of the patient. In addition, in particular embodiments, the depth of the slot in the needle guide is non-uniform over the length of the slot. The non-uniform depth allows a plane to be formed in which the needle may be tilted and aligned, but also allows more of the needle to be exposed in order to facilitate handling by a medical professional conducting the imaging analysis. In some implementations the depth of the slot is greatest at the portion of the slot proximate the patient, while in other implementations the depth of the slot is greatest at the portion of the slot substantially intermediate the ends of the slot, while in still other implementations the depth of the slot is greatest at the portion of the slot distal from the patient.

The distance between the interior surfaces of the slot can be varied in order to allow the slot to accommodate a variety of widths of needle. The slot can be narrow to accommodate a narrow needle, or wide to accommodate a wide needle. The variation of slot width can be accomplished by, for example, insertion of a separate piece into the slot to narrow it, or by having the width of the slot mechanically varied by being screwed or clamped to determine different slot dimensions.

In specific implementations, the needle guide system includes a bracket and a mounting base in addition to the actual needle guide. The mounting base secures the needle guide to the bracket, and the bracket secures the mounting base to an imaging instrument, such as an ultrasonic probe. While the bracket may be separable from the probe, it may also be integrally formed thereto and in essence be one piece with the probe.

The needle guide system of the present invention is designed such that it may be used with a protective cover placed over the bracket and mounting base. The needle guide is configured to be removably secured to the mounting base over the protective cover, without the development of significant kinetic friction between the protective cover and the needle guide during mounting and removal of the needle guide. As such, the disposable needle guide may be placed on the mounting base, and removed therefrom, with minimal mechanical stress to the protective cover, thereby preventing holes in the protective cover from developing and maintaining a sterile environment around the imaging instrument.

In specific implementations of the present invention, the needle guide further includes a movable locking member having an unlocked configuration in which the locking member does not apply pressure to the mounting base, while also having a locked configuration in which the locking member does apply pressure to the mounting base. The locking member may be alternated between a locked and an unlocked configuration without applying significant kinetic friction to the protective cover.

In certain implementations, the bracket of the present invention includes two paired arms for securing the needle guide system to an imaging instrument in specific implementations. As noted above, the bracket may be integrally formed with the imaging instrument to be one piece. The paired arms are configured to apply a compressive force to the imaging instrument, and the imaging instrument is an ultrasonic probe in specific implementations.

The above summary of the present invention is not intended to describe each discussed embodiment of the present invention. This is the purpose of the figures and the detailed description which follow.

BRIEF DESCRIPTION OF THE DRAWINGS

Other aspects and advantages of the invention will become apparent upon reading the following detailed description and references to the drawings, in which.

While the invention is susceptible to various modifications and alternative forms, specifics thereof have been shown by way of example and drawings, and will be described in detail. It should be understood, however, that the intention is not to limit the invention to particular embodiments described. On the contrary, the intention is to cover modifications, equivalents, and alternatives falling within the spirit and scope of the invention as defined by the appended claims.

DETAILED DESCRIPTION

Figure 1:
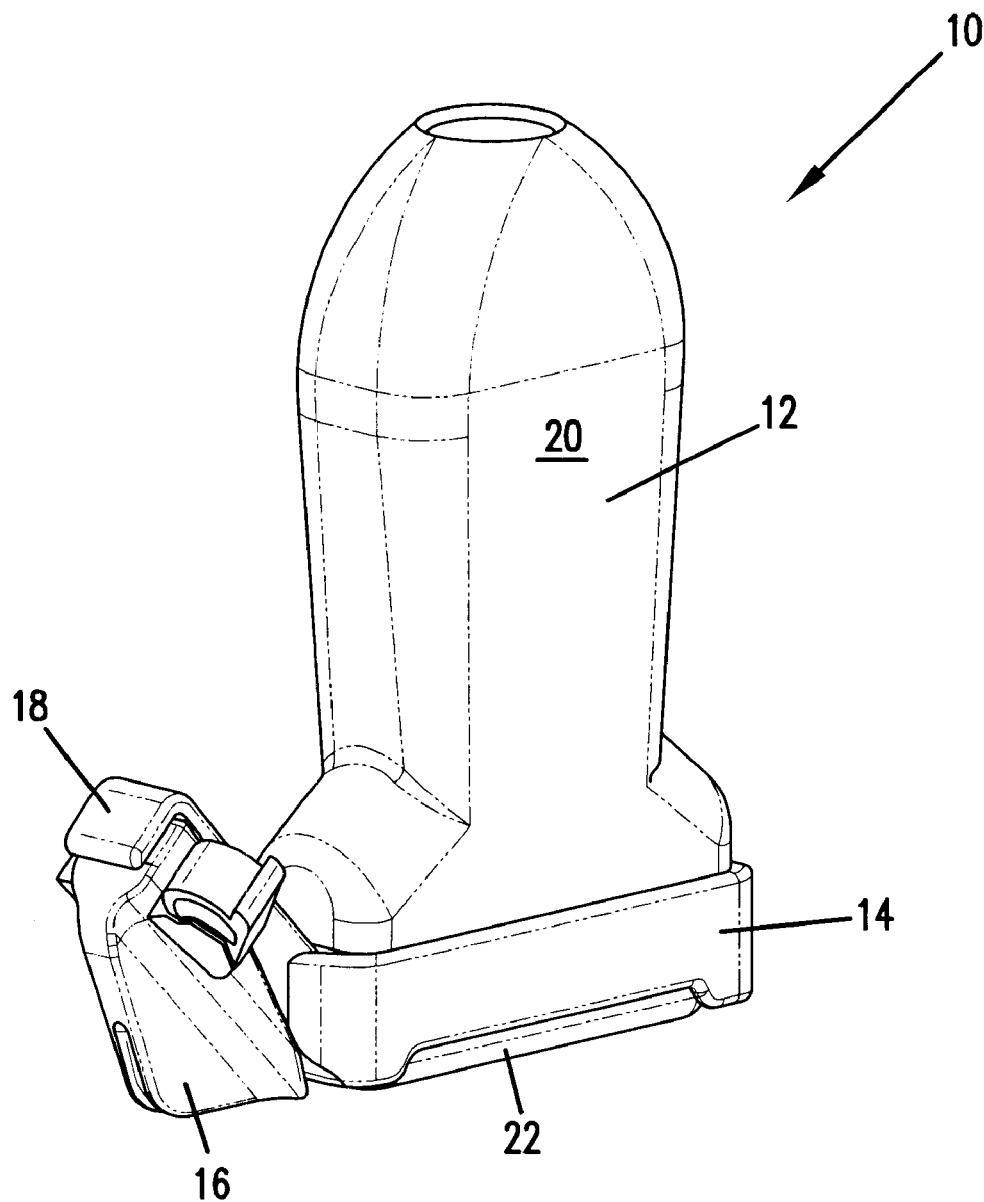
FIG. 1 is a perspective view of a needle guide system constructed in accordance with the present invention, showing the needle guide installed on an ultrasonic probe.

Referring now to the figures wherein like numerals identify like elements throughout the different views, FIG. 1 shows a perspective view of a needle guide system constructed in accordance with the present invention. Needle guide system 10 includes an ultrasound probe 12 onto which is secured a bracket 14. A needle guide 16 is fitted onto a mounting base portion 18 of the bracket 14.

Ultrasound probe 12 includes a handle 20 connected to a sensor 22. Handle 20 is typically configured to be grasped by the hand of a medical practitioner who is conducting an imaging analysis with the ultrasound probe 12 (or other medical imaging instrument). However, the handle 20 may alternatively be held by a mechanical brace or adjusting device for holding the ultrasound probe in a specific adjustable position. The sensor 22 includes an ultrasound transducer and receiver that sends out and receives sound waves that are transmitted to diagnostic and display equipment (not shown).

Figure 2:
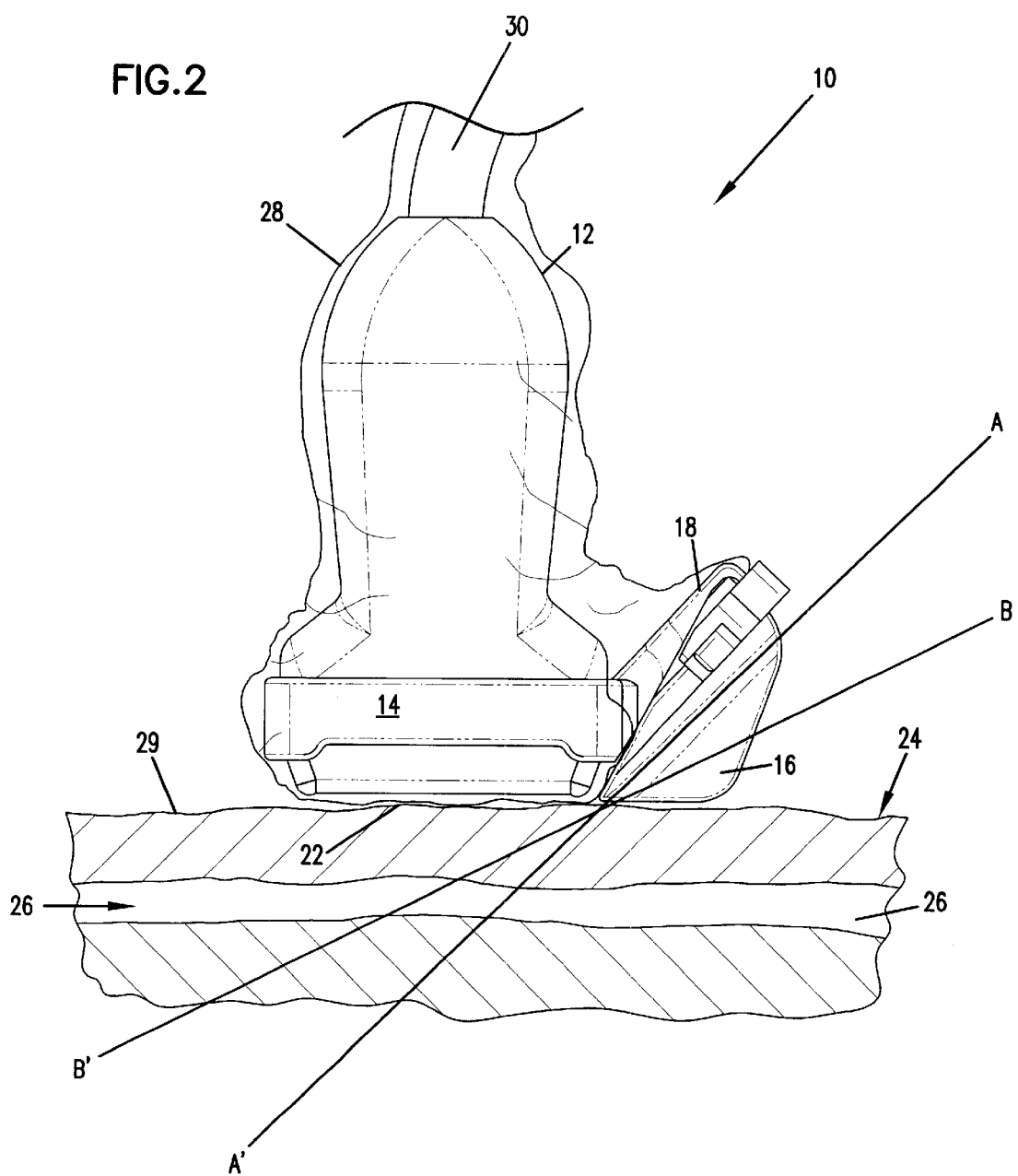
FIG. 2 is a side elevational view of a needle guide system constructed in accordance with the present invention, showing two angles of orientation for a needle as well as a cross section of the skin of a patient.

Referring now to FIG. 2, the ultrasound probe 12 may be placed in a position proximate a patient 24. In FIG. 2, patient 24 is depicted in fractional view showing a target zone 26 and an outer surface or skin 29. Target zone 26 may be any of a number of locations within the body of a human or animal which is desirably accessed by a needle or other thin medical instrument, such as a catheter or biopsy probe. For example, as shown in FIG. 2, target zone 26 may be a vein or artery. Target zone 26 can also be a tumor of which a biopsy sample is desired, or a volume of amniotic fluid from which a sample is desired.

FIG. 2 also shows a protective cover 28 positioned over the outside of the probe 12. Protective cover 28 provides a sterile seal over the ultrasound probe 12, bracket 14, and mounting base 18 such that these elements of the needle guide system 10 remain free of contamination during most medical procedures. As such, the enclosed elements of the needle guide system 10 do not come in contact with bodily fluids and reduce the risk of transfer of disease-causing vectors between the needle guide system 10 and the patient 24.

The protective cover 28, which is normally disposable, thereby prevents contamination between patients as well as provides a low-cost method of reducing sterilization requirements of the ultrasound probe and needle guide system. The needle guide 16 is outside of the protective cover, and therefore can be disposed of after the medical procedure or sterilized using conventional methods.

Protective cover 28 is normally constructed of a thin polymer film, most often of natural or synthetic latex. While protective cover 28 will normally encompass the entire ultrasound probe, bracket 14 and needle guide mounting base 18, it is preferred that it include an opening at a cable terminus 30. Cable terminus 30 leads to the diagnostic and display equipment (not shown).

Bracket 14 is configured to securely retain the mounting base 18 and needle guide 16 to the ultrasound probe 12. While bracket 14 may have any of numerous configurations suitable for securing mounting base 18 and needle guide 16 to the ultrasound probe 12, in at least one implementation bracket 14 has arms on opposite sides of the ultrasound probe 12. The arms fit around opposing sides of the sensor 22 of the ultrasound probe 12 and provide a compressive force securing mounting base 18 and needle guide 16 by way of the bracket 14 to the ultrasound probe 12.

The needle guide mounting base 18, mentioned above, is the portion of the needle guide system 10 to which the needle guide 16 is secured or mounted to the mounting base 18. In certain implementations of the present invention, the needle guide 16 and mounting base 18 are integrally formed to one another. However, in other implementations, the needle guide 16 and mounting base 18 are separated from one another by the protective cover 28. In these implementations, the needle guide 16 is removable from the mounting base 18. In certain such implementations, the needle guide 16 is disposable, while the mounting base 18 and bracket 14 are reused for multiple imaging procedures. While needle guide 16 may be disposable, it will be appreciated that even a "disposable" needle guide may be reused for more than one imaging analysis on the same patient, or may be sterilized between patients, if desired.

Alternatively, a new needle guide 16 is used for each medical procedure. It will be appreciated that the needle guide 16, consisting of a relatively small piece compared to the rest of the needle guide system 10, can have a reduced cost to use compared to needle guide systems that have a large disposable piece. The cost savings may come in the form of reduced materials, but more significantly can come from having reduced cleaning and sterilization costs and cost savings coming from the reuse of essential components, particularly the mounting base 18, for multiple procedures.

FIG. 2 also depicts two different example needle paths, identified as A–A' and B–B', that a needle can occupy. Path A–A', for example, can be the path of the needle during insertion to pierce the skin, while path B–B' can be the path of the same needle after it has been directed downward and into a target, such as a vein or artery. As shown in the figures, the needle can have the angle altered after it enters the skin.

Alternatively, paths A–A' and B–B' represent two different paths taken by two separate needles using the same needle guide and without alteration of the guide or its position. Thus, one advantage of the present invention is that it allows the needle to be placed at multiple angles without modification of the needle guide. For example, a first needle could be placed at an angle of 15 degrees to the skin. A second needle could be placed at a different position on the patent at an angle of 30 degrees to the skin. A third needle could be placed at yet a third position at another angle to the skin. All of these needle placements could be accomplished without modification or adjustment to the needle guide mechanism (other than possible slight relocation of the position on the patient).

Figure 3:
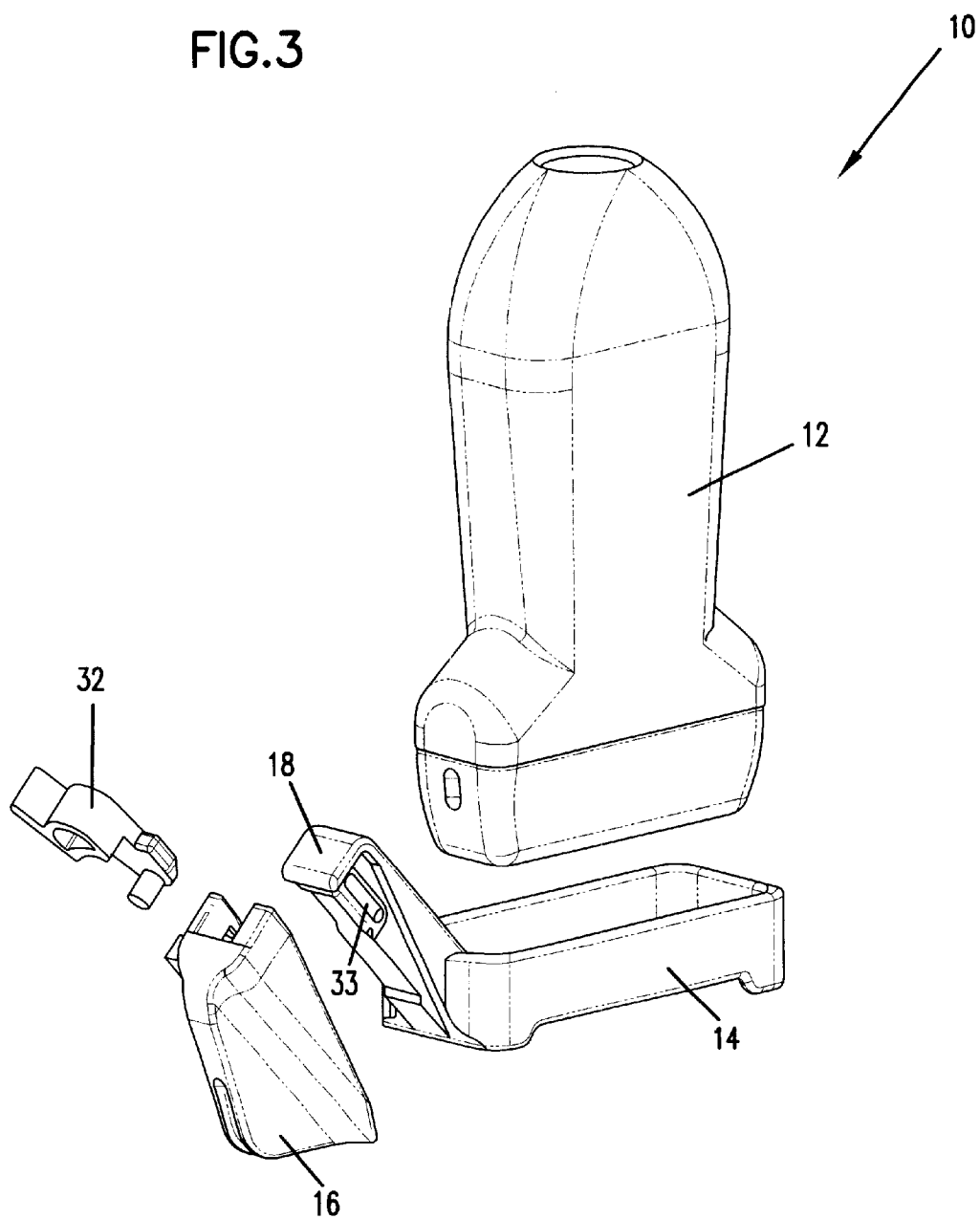
FIG. 3 is an exploded perspective view of a needle guide system constructed in accordance with the present invention.
Figure 4:
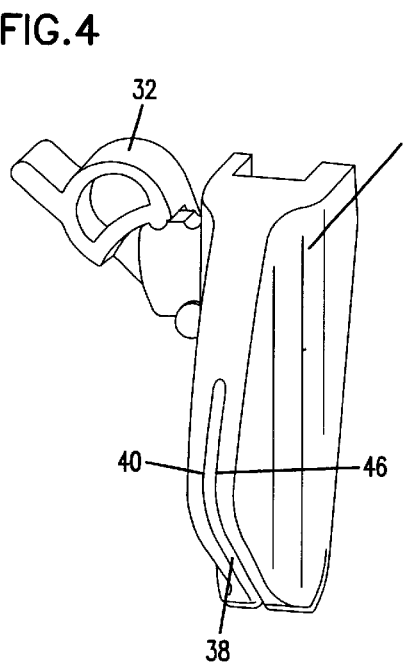
FIG. 4 is an enlarged perspective view of a needle guide constructed in accordance with the present invention.
Figure 5:
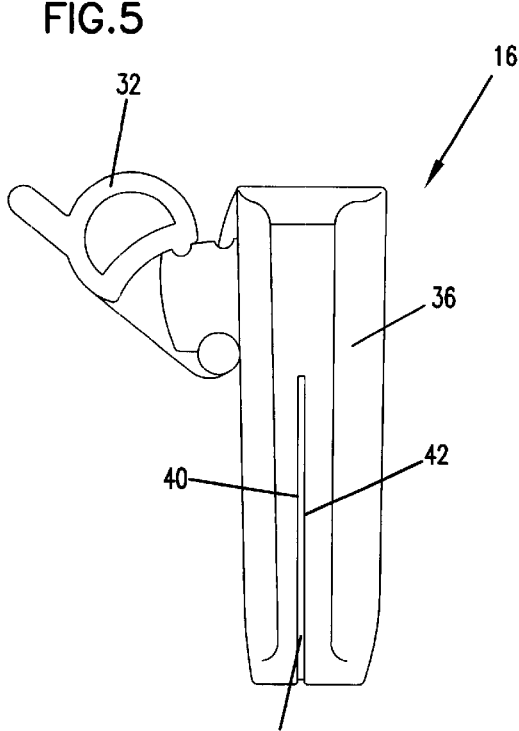
FIG. 5 is an enlarged front elevational view of a needle guide constructed in accordance with the present invention.
Figure 6:
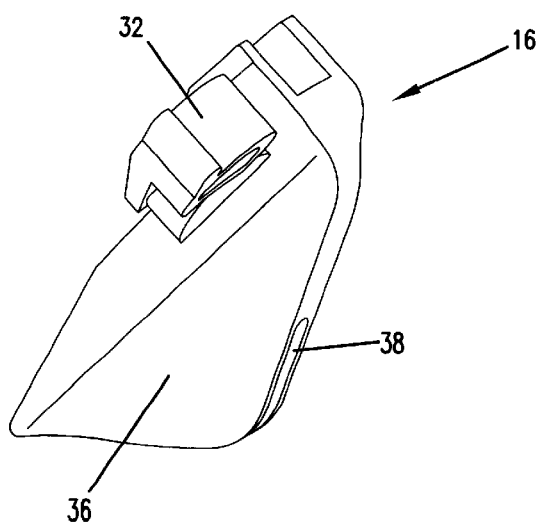
FIG. 6 is an enlarged side elevational view of a needle guide constructed in accordance with the present invention.

The manner in which the components of the needle guide system 10 are assembled is more clearly shown in FIG. 3. The ultrasound probe 12 fits into the bracket 14. The bracket 14 includes an integrally formed mounting base 18 onto which the needle guide 16 is attached. In addition, a locking member 32 is shown (and discussed below). The locking member 32 assists in retaining the needle guide 16 to the mounting base 18.

Now, referring to FIGS. 4, 5, 6, 7A and 7B, the needle guide 16 is shown to include a body 36 having a slot 38 into which may be placed a needle shaft. The slot 38 has two interior surfaces 40, 42 that are positioned opposite one another and combine to define a plane of movement in which a needle can pivot. A needle stays within this plane while being inserted into the patient, but can be freely tilted within the plane, and thus can take numerous angles relative to the surface of the skin.

In certain implementations, the plane of movement is substantially perpendicular to the surface of the skin of a patient. In addition, in particular embodiments, the depth of the slot 38 is non-uniform over the length of the slot. The variable depth allows a plane to form in which the needle may be tilted and aligned, but also allows more of the needle to be exposed in order to facilitate handling by a medical professional conducting the imaging analysis. In some implementations the depth of the slot 38 is greatest at the portion of the slot 38 proximate the patient, while in other implementations the depth of the slot 38 is greatest at the portion of the slot 38 substantially intermediate the ends of the slot, while in yet other implementations the depth of the slot is greatest at the portion of the slot distal from the patient.

The distance between the interior surfaces of the slot 38 can be varied in order to allow the slot to accommodate a variety of widths of needles. The slot 38 can be narrow to accommodate a narrow needle, or wide to accommodate a wide needle. The variation of slot width can be accomplished by, for example, insertion of a separate piece into the slot to narrow it, or by having a mechanically variable width slot that is screwed or clamped to determine different slot dimensions.

Figure 7A:
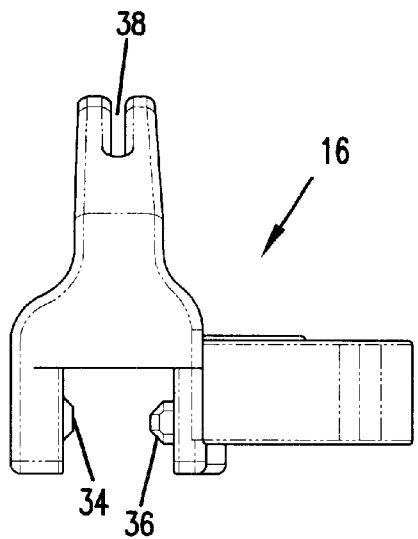
FIG. 7A is an enlarged top elevational view of a needle guide constructed in accordance with the present invention.
Figure 7B:
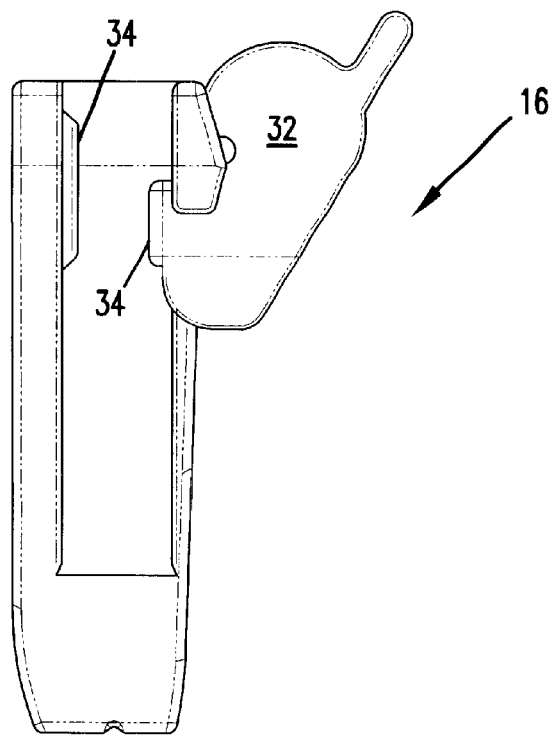
FIG. 7B is an enlarged rear elevational view of a needle guide constructed in accordance with the present invention.

In reference now to FIGS. 3, 7A and 7B, the portion of the mounting base 18 that is configured to receive the needle guide 16 will be described. The mounting base 18 is configured such that a needle guide 16 may be secured to the mounting base 18. In certain implementations of the present invention, the mounting base 18 permits the mounting of the needle guide 16 with minimal kinetic friction, and uses a compressive force to retain the needle guide 16. Kinetic friction refers herein to the friction generated when two surfaces move with respect to one another while in contact with one another.

The depth of the slot in the needle guide 16 is preferably significantly greater than the width. Thus, the slot is narrow but deep. In certain implementations, the depth of the slot measured at a first point at the exterior of the slot to the interior of the slot proximate is more than 3 times the width of the slot (the distance between the first and second surfaces). In certain implementations, this distance is greater than 5 times the width of the slot. It should be appreciated, however, that this distance need not be uniform along the entire length of the slot. To the contrary, what is important is that the slot define a plane of movement in which the needle may be tilted. It will be appreciated to one of skill in the art that the slot depth need not be uniform along the length of the slot to successfully form a plane of movement.

To avoid kinetic friction, the implementation shown includes a receiver recess 33, which is a shallow depression, generally uniform in depth, along the first sides of the mounting base. The back and top of the needle guide 16 is shown depicted in FIGS. 7A and 7B. Locking protrusions 34 in the needle guide 16 are configured to engage the receiver recesses 33 of the mounting base 18. One or more of the locking protrusions 34 is positioned on a locking member 32.

It will also be appreciated that in the present invention the retractable characteristic of the locking protrusions 34 of the locking member 32 allows for placement of a tight-fitting needle guide 16 over a protective cover 28 and mounting base 18 with low kinetic friction. Once in place over the mounting base, the locking member 32 is "locked" so as to press the two locking protrusions 34 into corresponding receiver recesses, thereby securely retaining the needle guide 16 to the base 18. The friction between the pieces is reduced because the locking protrusion on the locking member 32 is retracted during the attachment and removal process, thereby expanding the space between the protrusions until the member 32 is locked in place. This design reduces the amount of "dragging" between the needle guide 16 and the cover 28 and mounting base 18, thereby preventing binding and potential puncture or damage to the cover 28.

It will be appreciated that, although the implementation of the invention described above is directed to an ultrasound probe, the present device may be used with other non-invasive medical imaging systems, and is not limited to ultrasound probes. In addition, while the present invention has been described with reference to several particular implementations, those skilled in the art will recognize that many changes may be made hereto without departing from the spirit and scope of the present invention.

We claim:

1. A needle guide for guiding a needle into a patient during imaging analysis, the needle guide comprising:
    an imaging probe;
    a body configured to be positioned adjacent to a sensor of the imaging probe when the probe is in contact with a patient such that the probe is adapted to be in substantially direct contact with the surface of the patient; and
    a slot in the body configured to receive a needle shaft, the slot having first and second interior surfaces positioned opposite one another and configured to retain the needle shaft between the first and second surfaces along a length of the slot such that the needle is freely pivotable within the slot prior to and after entry of the needle into a patient, and such that the needle is not further retained within the slot except by the first and second surfaces;
    wherein the slot has a depth measured substantially perpendicular to the needle shaft and a distance measured between the first and second interior surfaces, the depth greater than the distance.

2. The needle guide for guiding a needle into a patient according to claim 1, wherein the slot defines a plane of movement in which the shaft of a needle may be adjusted during imaging analysis.

3. The needle guide according to claim 2, wherein the plane of movement is substantially perpendicular to the surface of the skin of a patient during imaging analysis.

4. The needle guide according to claim 1, wherein the depth of the slot is non-uniform over the length of the slot.

5. The needle guide according to claim 4, wherein the depth of the slot is greatest at the portion of the slot proximate a patient.

6. The needle guide according to claim 1, wherein the distance between the first and second surfaces is variable to accommodate needles of different diameters.

7. The needle guide according to claim 6, wherein the distance is varied by a clamping action.

8. The needle guide according to claim 1, wherein the portion of the slot closest to the surface of the skin of a patient is proximate a portion of the imaging instrument probe adjacent to the skin of the patient.

9. The needle guide according to claim 1, wherein the body is configured to be attached to a bracket secured to an imaging instrument.

10. A needle guide for guiding a needle into a patient during imaging analysis, the needle guide comprising:
    an imaging instrument;
    a body configured to be secured to the imaging instrument; and
    first and second extended members of the body, the first extended member having an interior, surface opposed to an interior surface of the second extended member, each of the interior surfaces including substantially planar portions;
    the substantially planar portions of the interior surfaces of the extended members combining to define a slot configured to receive a needle, the slot having a width between the planar portions and a depth substantially perpendicular to the width;
    wherein the width of the slot is substantially equal to the diameter of the needle and the depth of the slot is greater than the diameter of the needle such that the slot defines a plane of movement in which the needle may be adjusted without removal from the slot or the needle guide such that the needle is freely pivotable within the slot prior to and after entry into the patient, and such that the needle is not further retained within the slot except by the first and second extended members interior surface.

11. The needle guide according to claim 10, wherein the plane of movement is substantially perpendicular to the surface of the skin of a patient undergoing imaging analysis.

12. The needle guide according to claim 10, wherein the depth of the slot is non-uniform over a length of the slot.

13. The needle guide according to claim 10, wherein the depth of the slot is greatest at a portion of the slot proximate a patient.

14. The needle guide according to claim 10, wherein the distance between the interior surfaces is variable to accommodate needles of different diameters.

15. The needle guide according to claim 10, wherein the portion of the slot closest to the surface of the skin of a patient is proximate a portion of the imaging probe adjacent to the skin of the patient.

16. The needle guide according to claim 10, wherein the body is configured to be attached to a bracket secured to an imaging instrument.

17. A needle guide system for guiding a needle into a patient undergoing imaging analysis, the needle guide system comprising:

a bracket for securing the needle guide system to an imaging instrument;

a mounting base integral to the bracket;

a needle guide configured to be removably secured to the bracket at the mounting base, the needle guide configured to be positioned adjacent to a sensor of an imaging probe when the probe is in contact with a patient such that the probe is adapted to be in substantially direct contact with the surface of the patient, the needle guide including:

a body; and a slot in the body configured to receive a needle shaft, the slot having first and second interior surfaces positioned opposite one another and configured to retain the needle shaft between the first and second surfaces along a length of the slot such that the needle is freely pivotable within the slot prior to and after entry into a patient, and such that the needle is not further retained within the slot except by the first and second surfaces;

wherein the slot has a depth measured substantially perpendicular to the needle shaft and a distance measured between the first and second interior surfaces, the depth greater than the distance.

18. The needle guide for guiding a needle into a patient according to claim 17, wherein the slot defines a plane of movement in which the shaft of a needle may be adjusted during imaging analysis.

19. The disposable needle guide system of claim 17, wherein a protective cover may be placed over the bracket and mounting base, and the disposable needle guide is configured to be removably secured to the mounting base over the protective cover without the development of significant kinetic friction between the protective cover and the disposable needle guide.

20. The disposable needle guide system of claim 17, wherein the bracket comprises paired arms for securing the needle guide system to an imaging instrument, the paired arms configured to apply a compressive force to the imaging instrument.

21. The disposable needle guide system of claim 17, wherein the imaging instrument is an ultrasound probe.

22. A method for retaining and directing a needle during imaging analysis, the method comprising:

(a) providing a needle;

(b) providing a needle guide comprising:

(i) a body configured to be positioned adjacent to a sensor of an imaging probe when the probe is in contact with a patient such that the probe is adapted to be in substantially direct contact with the surface of the patient; and (ii) a slot in the body configured to receive a needle shaft, the slot having first and second interior surfaces positioned opposite one another and configured to retain the needle shaft between the first and second surfaces along a length of the slot, such that the needle is freely pivotable within the slot prior to and after entry of the needle into a patient, and such that the needle is not further retained within the slot except by the first and second surfaces; wherein the slot has a depth measured substantially perpendicular to the needle shaft and a distance measured between the first and second interior surfaces, the depth greater than the distance;

(c) inserting the needle into the needle guide;

(d) adjusting the angle of the needle in the slot of the needle guide.

23. The method according to claim 22, wherein the slot defines a plane of movement in which the shaft of a needle may be adjusted during imaging analysis.

24. The method according to claim 23, wherein the plane of movement is substantially perpendicular to the surface of the skin of a patient during imaging analysis.

* * * * *